(12) United States Patent
Tang et al.

(10) Patent No.: US 11,688,999 B2
(45) Date of Patent: Jun. 27, 2023

(54) NANO WATER ION GROUP GENERATOR (71) Applicant: Hangzhou Dazn Electromechanical Technology Co., Ltd., Hangzhou (CN)

(72) Inventors: Feng Tang, Hangzhou (CN); Zebin Wu, Hangzhou (CN); Chao Yuan, Hangzhou (CN); Xingjie Dai, Hangzhou (CN)

(73) Assignee: Hangzhou Dazn Electromechanical Technology Co., Ltd., Hangzhou (CN)

( * ) Notice: Subject to any disclaimer, the term of this patent is extended or adjusted under 35 U.S.C. 154(b) by 0 days.

(21) Appl. No.: 17/854,240

(22) Filed: Jun. 30, 2022

(65) Prior Publication Data
US 2023/0012035 A1 Jan. 12, 2023

(30) Foreign Application Priority Data
Jun. 30, 2021 (CN) .......................... 202110752171.X (51) Int. Cl.
*A61L 9/22* (2006.01)
*H01T 23/00* (2006.01)
*H10N 10/13* (2023.01)
*H10N 10/17* (2023.01)

(52) U.S. Cl.
CPC ................ *H01T 23/00* (2013.01); *A61L 9/22* (2013.01); *H10N 10/13* (2023.02); *H10N 10/17* (2023.02)

(58) Field of Classification Search
CPC .................................. A61L 9/22; H01T 23/00
See application file for complete search history.

(56) References Cited

U.S. PATENT DOCUMENTS

| | | | | |
|---|---|---|---|---|
| 2009/0001200 A1* | 1/2009 | Imahori | ................ | B05B 5/0533 239/690 |
| 2011/0005794 A1* | 1/2011 | Lee | .......................... | A61L 9/22 174/1 |

FOREIGN PATENT DOCUMENTS

| | | |
|---|---|---|
| CN | 109332030 A | 2/2019 |
| CN | 109980534 A | 7/2019 |
| CN | 210278744 U | 4/2020 |

* cited by examiner

*Primary Examiner* — Eliza W Osenbaugh-Stewart (57) ABSTRACT

The invention provides a nano water ion group generator, including: at least a pair of P/N-type semiconductor dies including P-type semiconductor dies and N-type semiconductor dies, with one end being a cooling end and the other end being a heating end; a heat absorption member for obtaining a cold energy generated by the cooling end and transferring the cold energy to a blocking member; the blocking member for conducting the cold energy to obtain moisture in a condensed water or an air with high relative humidity; an ionizing member to absorb, collect or accumulate moisture in the condensed water or the air with high relative humidity, and be electrically coupled to the high voltage power supply for further ionizing the air and the moisture around the ionizing member under the action of avalanche effect to obtain at least one nanometer-sized substance among charged particles and oxygen-containing radicals.

11 Claims, 5 Drawing Sheets

NANO WATER ION GROUP GENERATOR

FIELD OF THE INVENTION

The invention belongs to the field of disinfecting, epidemic prevention and healthy air, in particular, to a nano water ion group generator.

BACKGROUND OF THE INVENTION

Due to many advantages such as biological activity, small particle size, strong penetration ability, stable performance, sterilization and disinfection and deodorization, nano water ions have attracted more and more attention. The existing nano water ion generators or devices still have the following drawbacks:

(1) Poor stability in structure: the thermoelectric dies, P/N semiconductor dies or Peltier refrigeration units are electrically connected to the discharge electrodes and exposed to the outside air, and the discharge electrode is easily damaged by the impact of external factors under the action of leverage due to the certain length, which causes the P/N type semiconductor dies to be broken, peeled off or fractured and results in poor stability in structure, thereby greatly increasing the defective rate of the product.

(2) Low efficiency of device: it needs to be refrigerated to below the air dew point temperature, and the Peltier refrigeration unit has large resistance to heat conduction and electrical conduction, so that the low refrigeration efficiency increases the use cost and power consumption.

(3) Opposite electrodes and high voltage electrodes are required, which not only causes large dimension of the device, but also causes the charged particles to be adsorbed and reduces their release: since the thermoelectric dies, the P/N semiconductor dies or the Peltier refrigeration unit are electrically connected to the discharge electrode, the high voltage cannot be applied to the discharge electrode at the same time, which will cause the cooling effect of the thermoelectric dies to decrease, or even be damaged by high-voltage breakdown. The opposite electrodes or high voltage electrodes need to be provided to load a high voltage to form a high voltage electric field, thereby greatly increasing the dimension of the device. Meanwhile, normally, loading the high voltage or grounding with the opposite electrodes or high voltage electrodes is easy to adsorb the charged particles generated by the electron avalanche effect, which greatly reduces the release and limits the application scenarios.

(4) Unstable condensed water: in the air environment of high temperature or extremely low humidity (such as with a relative humidity less than 15%), the dew point temperature is extremely low, and it is difficult for thermoelectric dies or Peltier refrigeration units to condense and obtain condensed water under this condition, resulting in a decrease in the release of nano water ions.

The invention provides a nano water ion group generator, which can comprehensively solve the above problems, has a compact structure, is safe and reliable, realizes the miniaturization of the external size, and has high cooling and heat dissipation efficiency.

SUMMARY OF THE INVENTION

An objective of the invention is to provide a nano water ion group generator in view of the drawbacks in the prior art, which uses the Peltier thermoelectric effect to create the cold energy. Due to stable structure, small size and low power consumption, the nano water ion group generator does not need to add water and can be applied to various application scenarios.

To solve the above-mentioned technical problems, the invention adopts the following technical schemes.

A nano water ion group generator includes:

at least a pair of P/N-type semiconductor die, including a P-type semiconductor die and an N-type semiconductor die, with a first end being a cooling end and a second end being a heating end;

a heat absorption member, electrically coupled to the cooling end of the P/N-type semiconductor die for obtaining a cold energy generated by the cooling end and transferring the cold energy to a blocking member;

the blocking member, having a first side thermally coupled to the heat absorption member for conducting the cold energy obtained by the heat absorption member to obtain a condensed water or an air with high relative humidity and a second end provided with the ionizing member to isolate and protect the P/N-type semiconductor die and prevent leakage and discharge of a high voltage power supply; and an ionizing member, disposed at one side of the blocking member to absorb, collect or accumulate a moisture in the condensed water or the air with high relative humidity, and be electrically coupled to the high voltage power supply to load a high voltage electric field for further ionizing the air and the moisture around the ionizing member under the action of avalanche effect to obtain at least one nanometer-sized substance among charged particles and oxygen-containing radicals.

Further, the ionizing member includes a conductor and/or a water-absorbing material.

Further, the water-absorbing material includes a porous medium consisting of a fibrous shaped body, or a plurality of organic and/or inorganic fibers, and the water-absorbing material absorbs, collects or accumulates the moisture in the condensed water or the air with high relative humidity while forming a multi-channel discharge path.

Further, the conductor includes an ionizing member base portion and an ionizing member thimble portion; a cross-sectional area of the ionizing member base portion is larger than a cross-sectional area of the ionizing member thimble portion, and the ionizing member base portion is disposed on one side of the blocking member to absorb the moisture in the condensed water or the air with high relative humidity on the blocking member; the ionizing member thimble portion is far away from the blocking member for forming a local high voltage electric field, which is easy to ionize the surrounding air and moisture.

Further, the ionizing member and the blocking member are separated by a prescribed distance to sufficiently form an air environment with the condensed water or the high relative humidity between the ionizing member and the blocking member.

Further, the ionizing member absorbs, collects or accumulates the moisture in the condensed water or the surrounding air with high relative humidity between the ionizing member and the blocking member.

Further, an end of the ionizing member away from the blocking member is an ionizing end, and the ionizing end is a curved surface to easily form the multi-channel discharge path.

Further, the generator further includes a substrate, and the P/N-type semiconductor die penetrates through and is embedded into the substrate for protecting and packaging the P/N-type semiconductor die.

Further, the ionizing member is connected with a fixing member, and the fixing member is used for fixing the ionizing member.

Further, the blocking member includes a material with high dielectric constant or high thermal conductivity.

Further, the generator further includes a heat sink, and the heat sink is electrically coupled to the heating end of the P/N semiconductor die for obtaining a heat energy generated by the heating end and dissipating the heat energy.

Further, the heat sink includes a pair of heat sink conductors; the heat sink is used to provide power to the P/N-type semiconductor die on the one hand, and to conduct or dissipate the heat energy generated by the heating end of the P/N-type semiconductor die on the other hand.

Further, the substrate adjacent to the heat absorption member or the heat sink is provided with a singular annular cut-out, and the singular annular cut-out is used to isolate and dissipate the heat energy and to prevent a neutralization of the cold energy and heat energy while further isolating the high voltage power supply and preventing the leakage discharge.

Due to the adoption of the above technical schemes, the invention has the following beneficial effects:

The invention is a nano water ion group generator, and the P/N-type semiconductor die penetrates through and is embedded into the substrate for protecting and packaging the semiconductor die. Due to the protection and packaging of the substrate as well as the barrier of the blocking member, the semiconductor die may be prevented from breaking, falling off or breaking due to the impact of external factors, which increases the stability of the device. According to the actual measurement, the bonding strength between the P/N-type semiconductor die and the device is greatly increased, and the ability to resist external impact force is increased by 2-5 times.

The ionizing member includes a conductor or a water-absorbing material, and is disposed at one side of the blocking member, so as to absorb, collect or accumulate the moisture in the condensed water or the air with high relative humidity. The blocking member has a surface area with high thermal conductivity and a small thickness, allowing sufficient access to condensed water or air with high relative humidity on the larger surface of the blocking member (high relative humidity due to cooling of the surrounding air), which greatly reduces the resistance to thermal conduction; meanwhile, due to the provision of the water-absorbing material, the moisture in the surrounding air with high relative humidity may be absorbed and stored without cooling to below the dew point temperature of the air, or the surrounding air with high relative humidity may be directly ionized to stably produce nano water ions, which not only improves the cooling temperature and cooling efficiency and reduces the use cost and power consumption, but also may obtain nano-water ions stably in the air environment of high temperature or extremely low humidity (such as relative humidity less than 15%), thereby enhancing the adaptability of the device to the air environment.

The blocking member includes a material with high dielectric constant or high thermal conductivity, with one side thermally coupled to the heat absorption member for conducting the cold energy obtained by the heat absorption member to obtain a condensed water or an air with high relative humidity and the other end coupled to the ionizing member to isolate and protect the P/N-type semiconductor die and prevent leakage and discharge of a high voltage power supply. On the one hand, the blocking member is used to efficiently transmit the cold energy absorbed by the heat absorption member, and on the other hand forms a medium isolation layer, so that the ionizing members not electrically connected to the P/N-type semiconductor die, thereby directly loading high voltage on the ionizing member without the provision of the opposite electrodes or high voltage electrodes and greatly reducing the size of the device. At the same time, since the opposite electrodes or high voltage electrodes are not provided, the charged particles generated by the electron avalanche effect are not adsorbed, which increases the release of charged particles, so that the release of charged particles has been increased by more than 110 times, and the effect of sterilization and disinfection has also been enhanced.

A substrate adjacent to the heat absorption member or the heat sink is provided with a singular annular cut-out, and the singular annular cut-out is used to isolate and dissipate the heat energy and to prevent a neutralization of the cold energy and heat energy while further isolating the high voltage power supply and preventing the leakage discharge.

BRIEF DESCRIPTION OF THE DRAWINGS

Further description of the invention will be made below in combination with drawings.

DESCRIPTION OF THE INVENTION

In order that the objectives, technical schemes and advantages of the invention will become more apparent, the invention will be described in more detail with reference to the drawings and examples above. It should be understood that the specific embodiments described herein are only for illustrating but not for limiting the scope of the invention. Also, in the following description, descriptions of well-known structures and techniques are omitted to avoid unnecessarily obscuring the concepts of the invention.

Embodiment 1

Figure 1:
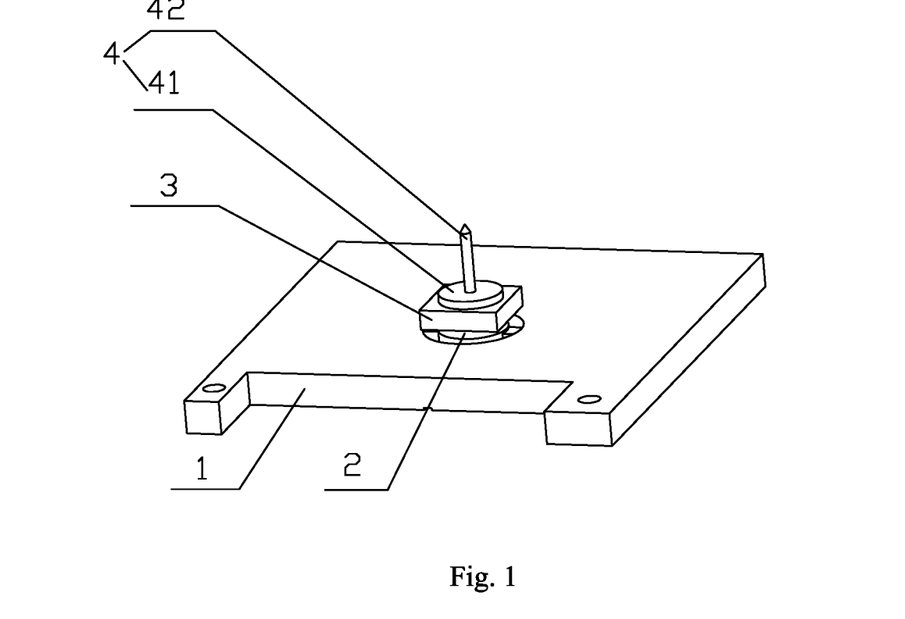
FIG. 1 is a front view three-dimensional diagram of a nano water ion group generator according to an embodiment of the invention.
Figure 2:
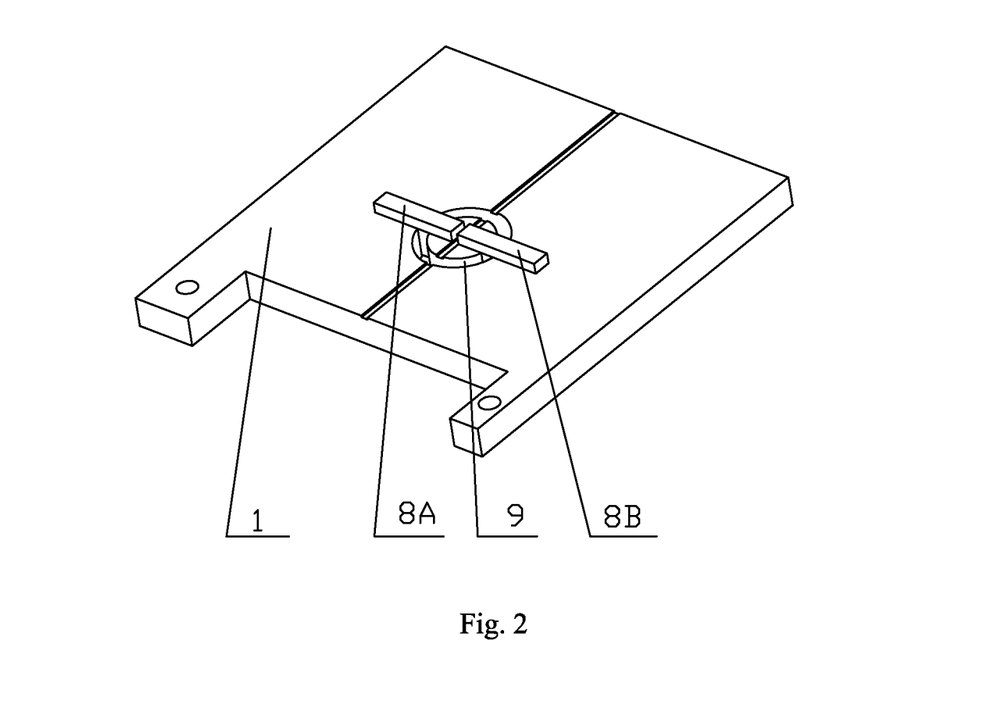
FIG. 2 is a back view three-dimensional diagram of the nano water ion group generator according to an embodiment of the invention.
Figure 3:
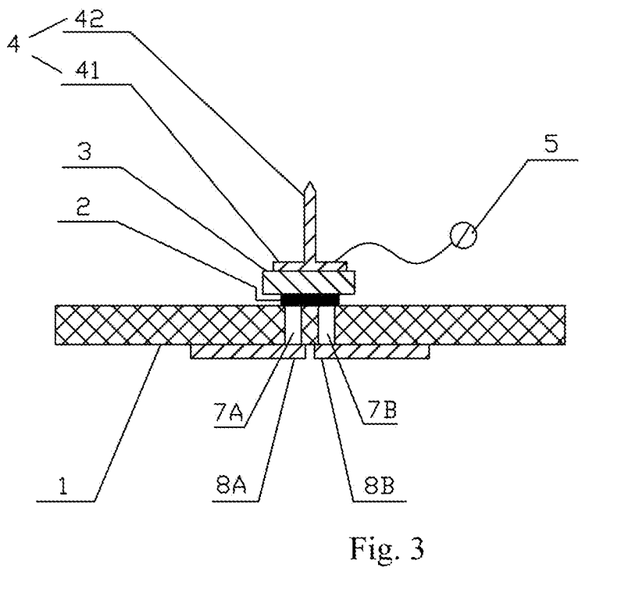
FIG. 3 is a cross-sectional diagram of the nano water ion group generator according to Embodiment 1 of the invention.

With reference to FIGS. 1 to 3, a nano water ion group generator according to an embodiment of the invention has main components including a heat absorption member 2, an N-type semiconductor die 7A, a P-type semiconductor die 7B, a heat sink 8, a blocking member 3, a high voltage power supply 5 and a substrate 1.

As a further description of this embodiment, there is at least one pair of P/N-type semiconductor die 7, and the pair of P/N-type semiconductor die 7 includes a P-type semiconductor die 7B and an N-type semiconductor die 7A, wherein a first end of the P/N-type semiconductor die 7 is a cooling end for obtaining a temperatures lower than the ambient temperature under the action of the thermoelectric effect, i.e., a cold energy, and a second end of the P/N-type semiconductor die 7 is a heating end for obtaining a temperatures higher than the ambient temperature under the action of the thermoelectric effect, i.e., a heat energy.

In this embodiment, the heat absorption member 2, the heat absorption member 2 is electrically coupled to the cooling end of the P/N-type semiconductor die 7 for obtaining the cold energy generated by the cooling end and transferring the cold energy to the blocking member 3.

In this embodiment, the blocking member 3, the blocking member 3 has a first side thermally coupled to the heat absorption member 2 for conducting the cold energy obtained by the heat absorption member 2 to obtain a condensed water or an air with high relative humidity 11, and the blocking member 3 has a second end provided with the ionizing member to isolate and protect the P/N-type semiconductor die and prevent leakage and discharge of a high voltage power supply 5.

As a further description of this embodiment, the blocking member 3 is used to form a dielectric isolation layer to isolate and protect the P/N semiconductor die and prevent leakage and discharge of the high voltage power supply 5, which otherwise may lead to a decrease in the cooling effect of the P/N semiconductor die and may be damaged by high voltage breakdown. The blocking member 3 includes a material with high dielectric constant or high thermal conductivity, such as alumina, ceramics, quartz, epoxy resin, etc.

As a further description of this embodiment, the ionizing member is disposed at one side of the blocking member 3 to absorb, collect or accumulate a moisture in the condensed water or the air with high relative humidity 11, and be electrically coupled to the high voltage power supply 5 to load a high voltage electric field for further ionizing the air and the moisture around the ionizing member under the action of avalanche effect to obtain at least one nanometer-sized substance among charged particles and oxygen-containing radicals. The formed nanometer-sized substance is a nano water ion group.

As a further description of this embodiment, the nano water ion group generator further includes a substrate 1, and the P/N-type semiconductor die 7 penetrates through and is embedded into the substrate 1 for protecting and packaging the P/N-type semiconductor die 7 while preventing the P/N-type semiconductor die from being fractured, fallen off, broken or corroded.

As a further description of this embodiment, the nano water ion group generator further includes a heat sink 8, and the heat sink 8 is electrically coupled to the heating end of the P/N semiconductor die 7 for obtaining a heat energy generated by the heating end and dissipating the heat energy.

As a further description of this embodiment, the heat sink 8 includes a pair of heat sink conductors, i.e., a heat sink 8 conductor 8A and a heat sink 8 conductor 8B; the heat sink 8 is used to provide power to the P/N-type semiconductor die 7 on the one hand, and to conduct or dissipate the heat energy generated by the heating end of the P/N-type semiconductor die 7 on the other hand.

Further, the pair of heat sink conductors, i.e., a heat sink 8 conductor 8A and a heat sink 8 conductor 8B, is integrally formed, and the material between them is an insulating material, so that they are not electrically connected to each other, and the components of the nano water ion group generator are less and more integrated.

As a further description of this embodiment, this embodiment adopts a first ionizing member 4, and the first ionizing member 4, which includes the conductors, is provided at one side of the blocking member 3 to absorb, collect or accumulate a moisture in the condensed water or the air with high relative humidity 11 on the one hand, and be electrically coupled to the high voltage power supply 5 to load a high voltage electric field for further ionizing the air and the moisture around the ionizing member under the action of avalanche effect to obtain at least one nanometer-sized substance among charged particles and oxygen-containing radicals on the other hand, wherein the formed nanometer-sized substance is a anemometer water ion group.

In this embodiment, the conductor includes an ionizing member base portion 41 and an ionizing member thimble portion 42. A cross-sectional area of the ionizing member base portion 41 is larger than a cross-sectional area of the ionizing member thimble portion 42, and the ionizing member base portion 41 is provided on one side of the blocking member 3 to absorb the moisture in the condensed water or the air with high relative humidity 11 on the blocking member 3. The ionizing member thimble portion 42 is far away from the blocking member 3 for forming a local high voltage electric field, which is easy to ionize the surrounding air and moisture.

In this embodiment, the first ionizing member 4 is thermally coupled to the blocking member 3 by way of such as welding to absorb, collect or accumulate the moisture in the condensed water or the air with high relative humidity 11 on the blocking member 3 while effectively absorbing the cold energy on the blocking member 3 to cool down the temperature of the first ionizing member 4, wherein the air with high relative humidity and even the condensed water may be directly obtained in and around the first ionizing member 4.

As a further description of this embodiment, the substrate 1 adjacent to the heat absorption member 2 or the heat sink 8 is provided with a singular annular cut-out 9, and the singular annular cut-out 9 is used to isolate and dissipate the heat energy for preventing a neutralization of the cold energy and the heat energy while maximizing the heat dissipation effect of natural convection or radiation, so that the nano water ion group generator achieves the best cooling effect. At the same time, the high voltage power supply 5 is further isolated to prevent leakage discharge.

Due to the protection and packaging of the substrate 1 as well as the barrier of the blocking member 3, the P/N-type semiconductor die may be prevented from breaking, falling off or breaking due to the impact of external factors, which increases the stability of the device. According to actual measurements, the bonding strength between the P/N-type semiconductor die and the device is greatly increased, and the ability to resist external impact force is increased by 2-5 times.

If the blocking member 3 is not provided, the first ionizing member 4 is electrically connected to the heat absorption member 2 and is further electrically connected to the P/N type semiconductor die. At this time, a high voltage is loaded on the first ionizing member 4, so that when an absolute value of the high voltage exceeds 100V, the P/N-type semiconductor die will no longer be cooled, or even be damaged by breakdown, thereby appearing serious leakage and discharge. Due to the provision of the blocking member 3 (such as ceramic or alumina with high dielectric constant), the P/N-type semiconductor die may maintain normal operation and cooling without leakage and discharge even if the absolute value of the high voltage loaded on the first ionizing member 4 reaches 10 kV.

Optionally, only the part of the heat absorption member 2 connected to the P-type semiconductor die 7B and the N-type semiconductor die 7A is made of conductor material, and the rest of the heat absorption member is made of insulating material with high thermal conductivity, such as ceramics.

Optionally, only the part of the heat sink 8 connected to the P-type semiconductor die 7B and the N-type semiconductor die 7A is made of conductor material, and the rest of the heat sink is made of insulating material with high thermal conductivity, such as ceramics.

Optionally, the heat absorption member 2 is in a circular shape, and may also be in a folded line shape, a square shape, etc., to meet different application scenarios.

Optionally, the heat sink 8 is in a sheet shape, and may also be in the folded line shape, a rib shape, etc., to meet different application scenarios.

Optionally, the blocking member 3 is in a circular shape, and may also be in the folded line shape, the square shape, etc., to meet different application scenarios.

Embodiment 2

Figure 4:
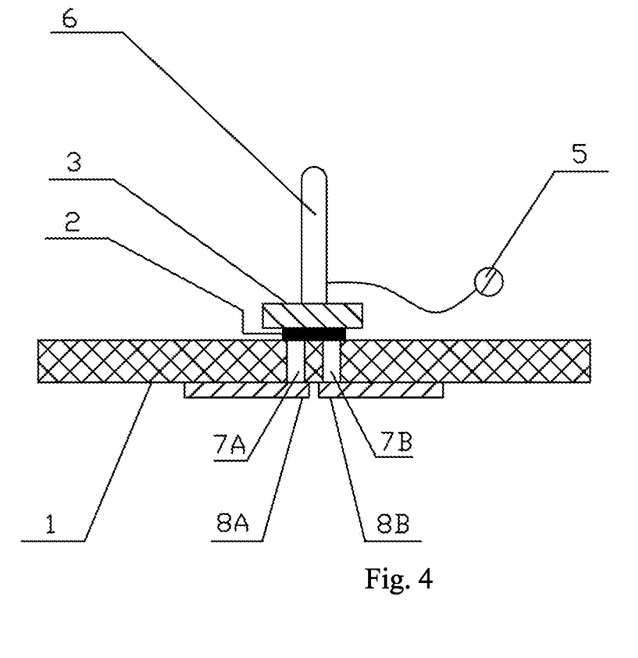
FIG. 4 is a cross-sectional diagram of the nano water ion group generator according to Embodiment 2 of the invention.

The difference between Embodiment 2 and Embodiment 1 is that: with reference to FIG. 4, Embodiment 2 adopts a second ionizing member 6, and the second ionizing member 6 is a water-absorbing material. The water-absorbing material includes a porous medium consisting of a fibrous shaped body, or a plurality of organic and/or inorganic fibers, and the water-absorbing material absorbs, collects or accumulates the moisture in the condensed water or the air with high relative humidity 11 while forming a multi-channel discharge path.

In this embodiment, the second ionizing member 6 is thermally coupled to the blocking member 3 to absorb or accumulate the cold energy, the moisture in the condensed water or the air with high relative humidity on the blocking member 3 while lowering the temperature of the second ionizing member 6 to further form an air environment with high relative humidity in and around the second ionizing member 6.

An end of the second ionizing member 6 away from the blocking member 33 is an ionizing end, and the ionizing end is a curved surface to easily form the multi-channel ionizing or discharge path.

In this embodiment, the second ionizing member 6 may be made of conductive material or non-conductive material. When the second ionizing member 6 is a non-conductor material, due to the adsorption of the condensed water or the air with high relative humidity 11, the second ionizing member 6 has the property of a conductor under the ionization action of the high-voltage electric field.

Embodiment 3

Figure 5:
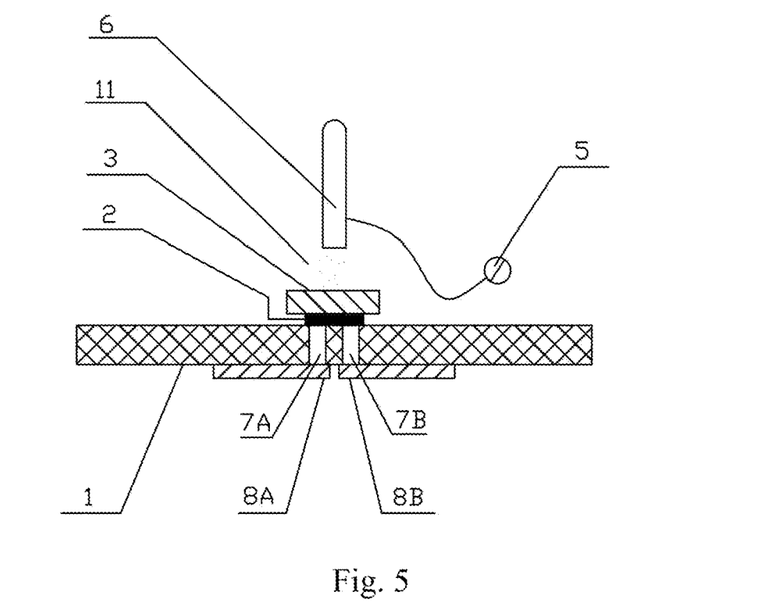
FIG. 5 is a cross-sectional diagram of the nano water ion group generator according to Embodiment 3 of the invention.

The difference between Embodiment 3 and Embodiment 1 is that: as shown in FIG. 5, the second ionizing member 6 and the blocking member 3 are separated by a prescribed distance to sufficiently form the condensed water or the air with high relative humidity 11 between the second ionizing member 6 and the blocking member 3, so as to absorb, collect or accumulate the moisture in the condensed water or the surrounding air with high relative humidity 11 on the blocking member 3.

The high voltage power supply 5 is electrically coupled to the second ionizing member 6 through the wire.

Figure 8:
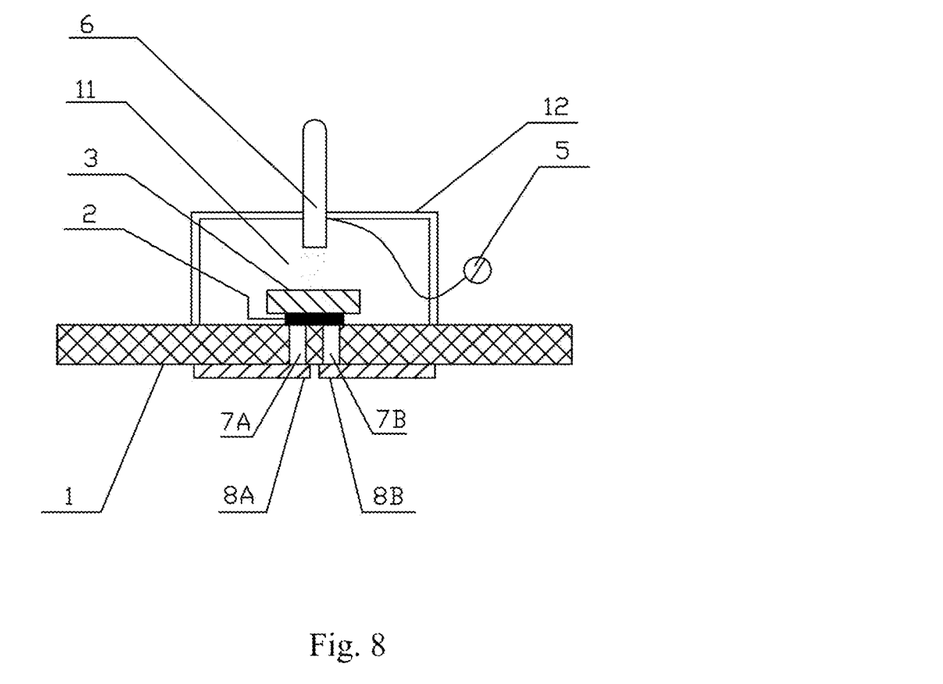
FIG. 8 is a cross-sectional diagram of providing a fixing member in the nano water ion group generator according to Embodiment 3 of the invention.

With reference to FIG. 8, in order to support and fix the second ionizing member 6, the second ionizing member 6 is connected with a fixing member 12, and the fixing member 12 may be connected to the substrate 1 to achieve the effect of supporting and fixing the second ionizing member 6.

Embodiment 4

Figure 6:
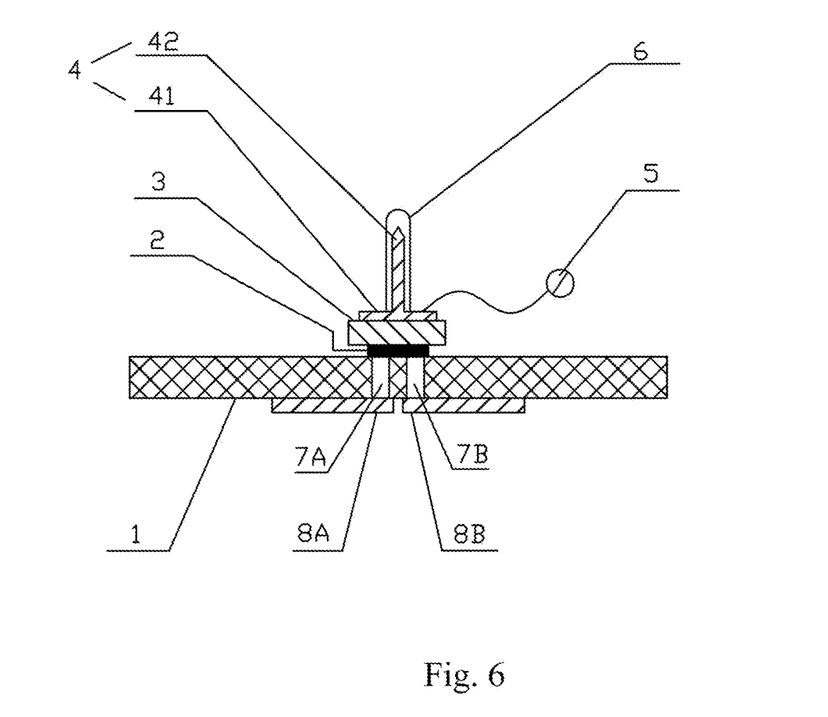
FIG. 6 is a cross-sectional diagram of the nano water ion group generator according to Embodiment 4 of the invention.

As a modification of Embodiment 3, as shown in FIG. 6, the first ionizing member 4 includes a conductor and a water-absorbing material. At this time, the ionizing member adopts both the first ionizing member 4 and the second ionizing member 6, and the second ionizing member 6 is made of the water-absorbing material. The water-absorbing material includes a porous medium.

The high voltage power supply 5 is electrically coupled to the first ionizing member 4 or the second ionizing member 6 through the wire. Preferably, when the second ionizing member 6 is a non-conductor material, which is more suitable for being electrically coupled to the first ionizing member 4.

The first ionizing member 4 is the conductor, and the first ionizing member 4 includes an ionizing member base portion 41 and an ionizing member thimble portion 42; a cross-sectional area of the ionizing member base portion 41 is larger than a cross-sectional area of the ionizing member thimble portion 42. The ionizing member base portion 41 is thermally coupled to the blocking member 3, and the ionizing member thimble portion 42 is embedded in the second ionizing member 6 to charge the second ionizing member 6 and support the second ionizing member 6 to absorb, collect or accumulate the cold energy, the moisture in the condensed water or the air with high relative humidity 11 on the blocking member 3 or the first ionizing member 4 while lowering the temperature of the second ionizing member 6 to further form an air environment with high relative humidity in and around the second ionizing member 6. Other features are the same as those in Embodiment 1 and Embodiment 3.

Embodiment 5

Figure 9:
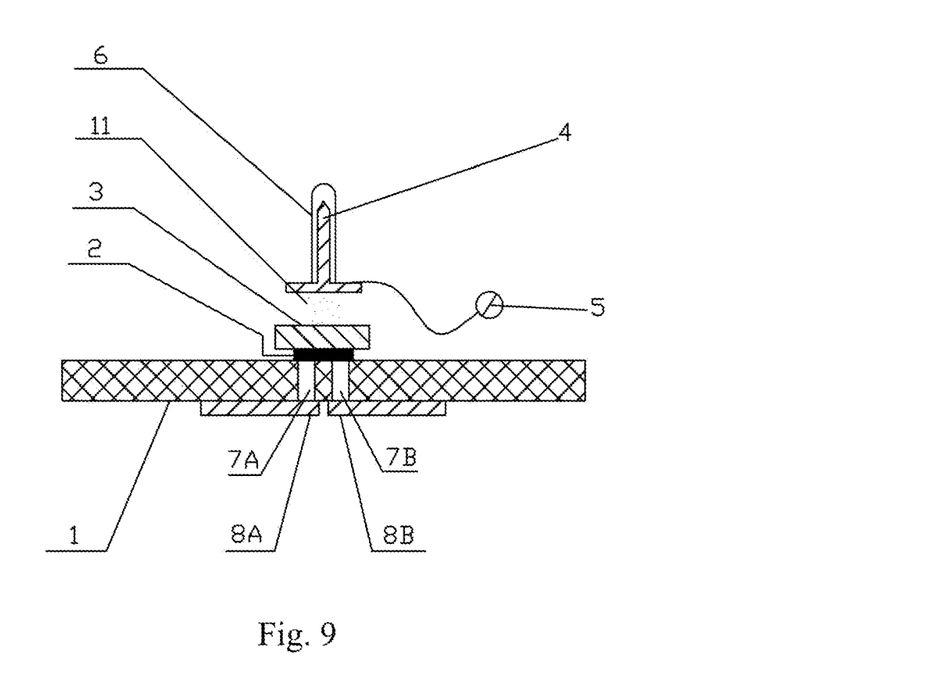
FIG. 9 is a cross-sectional diagram of the nano water ion group generator according to Embodiment 5 of the invention.

As an improved combination of Embodiment 3 and Embodiment 4, the first ionizing member 4 includes a conductor and a water-absorbing material. At this time, the ionizing member adopts both the first ionizing member 4 and the second ionizing member 6, and the second ionizing member 6 is made of the water-absorbing material. The water-absorbing material includes a porous medium. The ionizing member consisting of the water-absorbing material and the conductor as a whole, and is separated from the blocking member 3 by a prescribed distance, as shown in FIG. 9, so as to sufficiently form the condensed water or the air with high relative humidity 11 between the ionizing member and the blocking member 3, so as to absorb, collect or accumulate the moisture in the condensed water or the surrounding air with high relative humidity 11 on the blocking member 3.

The high voltage power supply 5 is electrically coupled to the first ionizing member 4 or the second ionizing member 6 through a wire. Preferably, when the second ionizing member 6 is a non-conductor material, it is more suitable for being electrically coupled to the first ionizing member 4.

Figure 7:
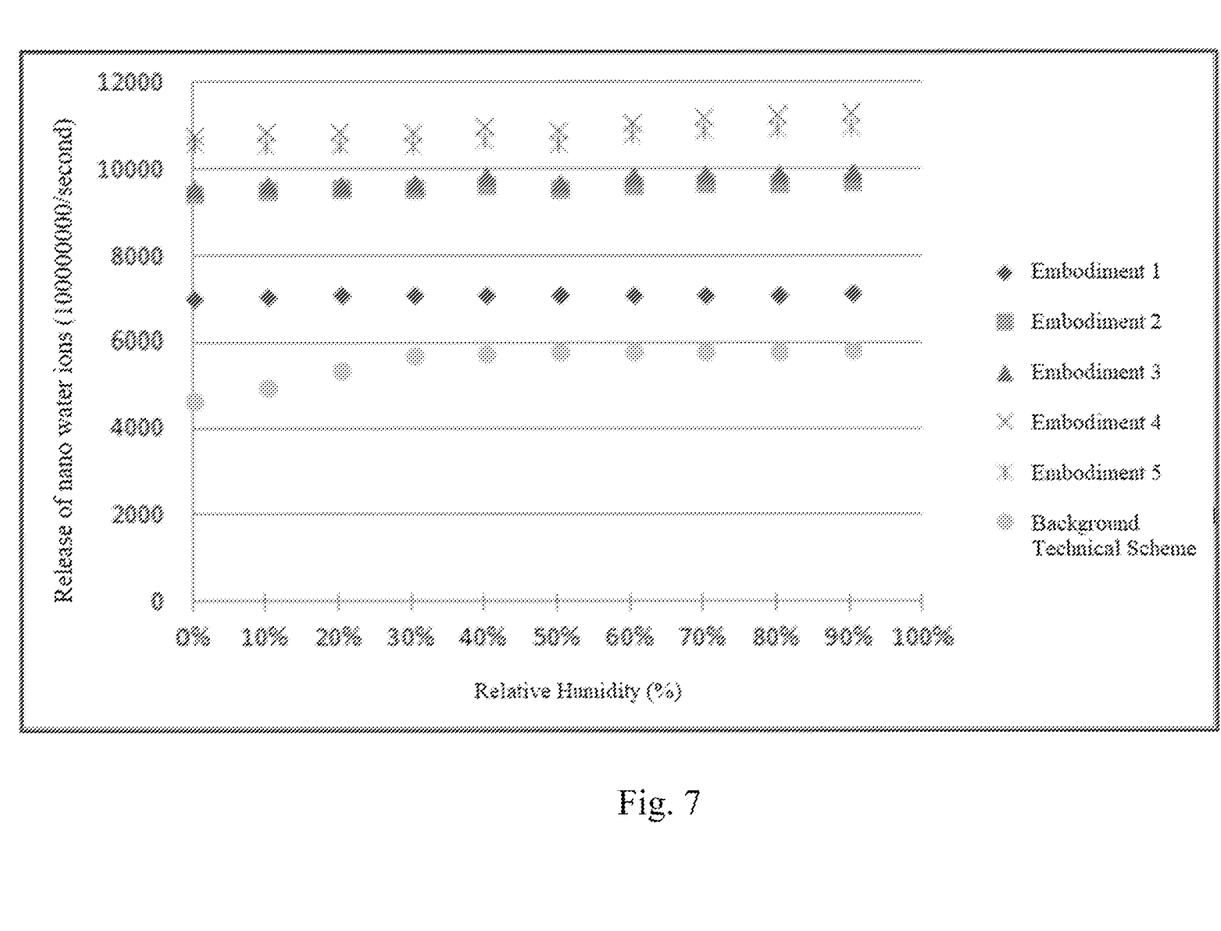
FIG. 7 is a comparison chart of the concentration of nano water ions released by the nano water ion generator under different relative humidity conditions.

Other experimental data are shown in Table 1 and FIG. 7:

TABLE 1

Experimental data table of different nano water ion generators (the ambient temperature is 25° C. and the relative humidity is 55%)

| Nano water ion generator | In the form of ionizing member or electrode | Loaded high voltage (kV) | Concentration of charged particles (10000/cm$^3$) | Release of nano water ions (100000000/second) | Device power (W) | Disinfection rate of corona virus (30m$^3$, 1h) |
|---|---|---|---|---|---|---|
| Embodiment 1 | Metal probe | −5.0 | 1320 | 7100 | 0.6 | 99.0% |
| Embodiment 2 | Porous water-absorbing material | −5.0 | 1140 | 9550 | 0.5 | 99.3% |
| Embodiment 3 | Porous water-absorbing material (separated by 2 mm) | −5.0 | 1110 | 9670 | 0.5 | 99.7% |
| Embodiment 4 | Metal probe + Porous water-absorbing material | −5.0 | 1170 | 10910 | 0.5 | 99.9% |
| Embodiment 5 | Metal probe + Porous water-absorbing material (separated by 2 mm) | −0.5 | 1150 | 10610 | 0.5 | 99.9% |
| Background technical scheme | Metal probe + Metal ring (opposite electrodes) | −5.0 | 10 | 5800 | 0.8 | 85.6% |

As can be seen from Table 1 and FIG. 7:

(1) Compared with the background technical scheme, due to the provision of the ionizing member consisting of a conductor or a water-absorbing material, which is disposed at one side of the blocking member 3, the moisture in the condensed water or the air with high relative humidity 11 is absorbed, collected or accumulated. The blocking member 3 has a surface area with high thermal conductivity and a small thickness, allowing sufficient access to condensed water or air with high relative humidity on the larger surface of the blocking member 3 (high relative humidity due to cooling of the surrounding air), which greatly reduces the resistance to thermal conduction. Meanwhile, due to the provision of the water-absorbing material, the moisture in the surrounding air with high relative humidity may be absorbed and stored without cooling to below the dew point temperature of the air, or the surrounding air with high relative humidity may be directly ionized to stably produce nano water ions, wherein the release of the nano water ions is increased by 22.4%-88%, which improves the cooling temperature and cooling efficiency and reduces the use cost and power consumption, and the device power is reduced by 25%-37.5%, so that the nano-water ions may be stably obtained even in the air environment of high temperature or extremely low humidity (such as relative humidity less than 15%) without interference, thereby enhancing the adaptability of the device to the air environment.

(2) The blocking member 3 includes a material with high dielectric constant or high thermal conductivity, with one side thermally coupled to the heat absorption member 2 for conducting the cold energy obtained by the heat absorption member 2 to obtain a condensed water or an air with high relative humidity and the other end coupled to the ionizing member to isolate and protect the P/N-type semiconductor die and prevent leakage and discharge of a high voltage power supply 5. On the one hand, the blocking member 3 is used to efficiently transmit the cold energy absorbed by the heat absorption member 2, and on the other hand forms a medium isolation layer, so that the ionizing members not electrically connected to the P/N-type semiconductor die, thereby directly loading high voltage on the ionizing member without the provision of the opposite electrodes or high voltage electrodes and greatly reducing the size of the device. At the same time, since the opposite electrodes or high voltage electrodes are not provided, the charged particles generated by the electron avalanche effect are not adsorbed, which increases the release of charged particles, so that the release of charged particles has been increased by more than 110 times, and the effect of sterilization and disinfection has also been enhanced.

The above are only specific embodiments of the invention, but the technical features of the invention are not limited thereto. Any simple changes, equivalent replacements or modifications made based on the invention in order to solve basically the same technical problems and achieve basically the same technical effects are all included in the protection scope of the invention.

What is claimed is:

1. A nano water ion group generator, comprising:
   at least a pair of P/N-type semiconductor die, comprising a P-type semiconductor die and an N-type semiconductor die, with a first end being a cooling end and a second end being a heating end;
   a heat absorption member, electrically coupled to the cooling end of the P/N-type semiconductor die for obtaining a cold energy generated by the cooling end and transferring the cold energy to a blocking member;
   the blocking member, having a first side thermally coupled to the heat absorption member for conducting the cold energy obtained by the heat absorption member to obtain a condensed water or an air with high relative humidity and a second side provided with an ionizing member to isolate and protect the P/N-type semiconductor die and prevent leakage and discharge of a high voltage power supply; and
   an ionizing member, disposed at one side of the blocking member to absorb, collect or accumulate the cold energy, a moisture in the condensed water or the air with high relative humidity, and be electrically coupled to the high voltage power supply to load a high voltage electric field for further ionizing the air and the moisture around the ionizing member under the action of avalanche effect to obtain at least one nanometer-sized substance among charged particles and oxygen-containing radicals;

wherein the ionizing member adopts both a first ionizing member and a second ionizing member, the first ionizing member is located above the blocking member, and the second ionizing member covers the first ionizing member;

wherein the first ionizing member comprises a conductor and/or a first water-absorbing material;

wherein the second ionizing member is made of a second water-absorbing material, and the first water-absorbing material and the second water-absorbing material each includes a porous medium.

2. The nano water ion group generator according to claim 1, wherein the conductor comprises an ionizing member base portion and an ionizing member thimble portion; a cross-sectional area of the ionizing member base portion is larger than a cross-sectional area of the ionizing member thimble portion, and the ionizing member base portion is disposed on one side of the blocking member to absorb the cold energy, the moisture in the condensed water or the air with high relative humidity on the blocking member; the ionizing member thimble portion is far away from the blocking member for forming a local concentrated electric field, which is easy to ionize the surrounding air and moisture.

3. The nano water ion group generator according to claim 1, wherein the ionizing member and the blocking member are separated by a prescribed distance to sufficiently form an air environment with the condensed water or the high relative humidity between the ionizing member and the blocking member.

4. The nano water ion group generator according to claim 3, wherein the ionizing member absorbs, collects or accumulates the moisture in the condensed water or the air with high relative humidity between the ionizing member and the blocking member.

5. The nano water ion group generator according to claim 4, wherein an end of the ionizing member away from the blocking member is an ionizing end, and the ionizing end is a curved surface to easily form the multi-channel discharge path.

6. The nano water ion group generator according to claim 1, further comprising a substrate, the P/N-type semiconductor die penetrates through and is embedded into the substrate for protecting and packaging the P/N-type semiconductor die.

7. The nano water ion group generator according to claim 1, wherein the ionizing member is connected with a fixing member, and the fixing member is used for fixing the ionizing member.

8. The nano water ion group generator according to claim 1, wherein the blocking member comprises a material with high dielectric constant or high thermal conductivity.

9. The nano water ion group generator according to claim 1, further comprising a heat sink, the heat sink is electrically coupled to the heating end of the P/N semiconductor die for obtaining a heat energy generated by the heating end and dissipate the heat energy.

10. The nano water ion group generator according to claim 9, wherein the heat sink comprises a pair of heat sink conductors; the heat sink is used to provide power to the P/N semiconductor die on the one hand, and to conduct or dissipate the heat energy generated by the heating end of the P/N semiconductor die on the other hand.

11. The nano water ion group generator according to claim 9, wherein a substrate adjacent to the heat absorption member or the heat sink is provided with a singular annular cut-out, and the singular annular cut-out is used to isolate and dissipate the heat energy and to prevent a neutralization of the cold energy and heat energy while further isolating the high voltage power supply and preventing the leakage discharge.

* * * * *